(12) United States Patent
John

(10) Patent No.: US 11,148,104 B1
(45) Date of Patent: Oct. 19, 2021

(54) SYSTEM FOR DISPENSING CONTROLLED AND SELECTIVE AMOUNTS OF CHEMICAL SALT COMPOSITIONS

(71) Applicant: Vlada John, Larchmont, NY (US)

(72) Inventor: Vlada John, Larchmont, NY (US)

( * ) Notice: Subject to any disclaimer, the term of this patent is extended or adjusted under 35 U.S.C. 154(b) by 148 days.

(21) Appl. No.: 16/284,357

(22) Filed: Feb. 25, 2019

Related U.S. Application Data

(60) Provisional application No. 62/635,042, filed on Feb. 26, 2018.

(51) Int. Cl.

| | | |
|---|---|---|
| *B01F 1/00* | (2006.01) | |
| *A61Q 19/10* | (2006.01) | |
| *A61K 8/23* | (2006.01) | |
| *A61K 8/02* | (2006.01) | |
| *E03C 1/046* | (2006.01) | |
| *A61K 33/06* | (2006.01) | |
| *B05B 1/18* | (2006.01) | |

(52) U.S. Cl.
CPC .......... *B01F 1/0033* (2013.01); *A61K 8/0204* (2013.01); *A61K 8/23* (2013.01); *A61K 33/06* (2013.01); *A61Q 19/10* (2013.01); *B01F 1/0016* (2013.01); *E03C 1/046* (2013.01); *A61K 2800/87* (2013.01); *A61K 2800/882* (2013.01); *B01F 2215/0031* (2013.01); *B01F 2215/0032* (2013.01); *B05B 1/18* (2013.01)

(58) Field of Classification Search
CPC ......... B05B 1/1636; B05B 1/18; B05B 1/185; B05B 7/244–2445; B05B 7/2462; B05B 13/0278; B05B 15/62; B05B 15/628; B05B 15/65–68; B01F 1/0033; B01F 1/0016; B01F 2001/0077; B01F 2001/0083; B01F 2001/0094; B01F 2215/0031; B01F 2215/0032; E03C 1/046; A61K 8/0204; A61K 8/23; A61K 33/06; A61K 2800/87; A61K 2800/882; A61Q 19/10; C02F 2307/06
USPC .......................... 239/9, 10, 58, 59, 315, 316
See application file for complete search history.

(56) References Cited

U.S. PATENT DOCUMENTS

| | | | | |
|---|---|---|---|---|
| 1,973,319 A | * | 9/1934 | Nelson ..................... | A47K 5/14 239/315 |
| 2,485,112 A | * | 10/1949 | Rose ..................... | B05B 7/2462 239/314 |
| 2,659,627 A | * | 11/1953 | McConnell .......... | E03C 1/0465 239/316 |

(Continued)

OTHER PUBLICATIONS

H. Atalar, et al. "External application of hypertonic salt solution for treatment of posttraumatic oedema." Acta Orthopaedica Belgica, vol. 71, No. 4 (Sep. 2005), pp. 472-476.

(Continued)

*Primary Examiner* — Cody J Lieuwen
(74) *Attorney, Agent, or Firm* — Rosenberg, Klein & Lee

(57) ABSTRACT

A chemical salt composition dispensing system allows chemical salt composition mixtures to be applied to a user. The dispensing system includes a mixing chamber releasing a mixture onto a user at a predetermined and controlled flow rate. The dispensing system may include one or two shelves mounted within a tubular container to permit flow through the first ring or flow through one sieve member to a second sieve member mounted below the first sieve member and further permits passage of the liquid flow onto the body of the user.

21 Claims, 10 Drawing Sheets

(56) References Cited

U.S. PATENT DOCUMENTS

| | | | | |
|---|---|---|---|---|
| 5,181,533 A | * | 1/1993 | Kooi | B01F 1/0016 |
| | | | | 137/268 |
| 2002/0070293 A1 | * | 6/2002 | Ti | E03C 1/046 |
| | | | | 239/317 |
| 2009/0101733 A1 | * | 4/2009 | Popov | B05B 7/2462 |
| | | | | 239/310 |
| 2010/0206799 A1 | * | 8/2010 | Leavitt | C02F 1/002 |
| | | | | 210/314 |

OTHER PUBLICATIONS

J. Gröber, et al. "Myth or Reality—Transdermal Magnesium?" Nutrients, vol. 9, No. 8 (Jul. 2017), p. 813. doi: 10.3390/nu9080813.
H. Laudańska, et al. "Permeability of human skin to selected anions and cations—in vitro studies." Research Communications in Molecular Pathology and Pharmacology, vol. 112, Nos. 1-4 (Feb. 2002), pp. 16-26.

* cited by examiner

SYSTEM FOR DISPENSING CONTROLLED AND SELECTIVE AMOUNTS OF CHEMICAL SALT COMPOSITIONS

REFERENCES TO RELATED APPLICATIONS

This application is based upon Provisional Application Ser. No. 62/635,042 filed on 26 Feb. 2018.

FIELD OF THE INVENTION

This invention is directed to the field of promoting wellness and personal care. This invention is further directed to the transdermal application of controlled and selective amounts of chemical salt compositions to the human body. Still further this invention is directed to the field of chemical salt composition dispensing systems for transdermal application to the body of a user. In particular, this invention relates to the field of providing dispensing systems for chemical salt compositions where hydroxide ions are transdermally applied to the body of a user. More in particular this invention is directed to the field of dispensing Magnesium Sulfate, commonly referred to as Epsom salts which produces hydroxide ions when dissolved in water. Still further, this invention relates to the technology of dispensing chemical salt compositions through the dermal layer of a user for promoting a balanced lifestyle where the ions enter the body through the skin of the user. More in particular, this invention relates to applying selective amounts of chemical salt compositions to the body of the user for aiding in exfoliation and promotion of new skin cell growth. Further this invention relates to the field of dispensing chemical salt compositions at a controlled rate and within specified time intervals to obtain the maximum effect of the transdermal application of the chemical salt compositions to the user's body. The invention is further directed to the field of chemical salt composition dispensing systems where the chemical salt composition can be maintained in a container in combination with essential oil solutions and then dispensed at a controlled rate to the body of a user. This invention is directed to the field of providing a dispensing system which is easily collapsible, lightweight, and transportable.

BACKGROUND OF THE INVENTION

Chemical salts are ionic compounds which can be formed by the neutralization reaction of an acid and a base. Chemical salts are composed of related number of cations so that the overall product is electrically neutral without a net charge. Such chemical salt compositions may be inorganic or organic. Epsom salt is commonly known as magnesium sulfate and has three differing forms, such as a heptahydrate, anhydrous and monohydrate form. The chemical compound includes sulfur/magnesium/oxygen. In its hydrate form, Epsom salt has a monoclinic crystal structure and the hydrate state is generally used for solution preparation, especially in medical preparations. Epsom salts appear similar to standard table salt, however, in medicinal use such is generally provided in larger salt crystals for use in, for example, bath water.

Numerous benefits for health/well-being have been reported with respect to positive effects of magnesium in Epsom salt. The Epsom salt breaks down into magnesium and sulfate with proponents of the practice believing that when a person soaks in an Epsom bath, the ions enter into the body transdermally.

There is support for the claim that both magnesium and sulfate ions, which are formed when magnesium sulfate is dissolved in water, can be transported through the skin. Transdermal application of such chemical salt compositions is thought to aid in a number of areas such as relief for stress and promotion of sleep.

Chemical salt compositions and, in particular, Epsom salts, are considered to be a good exfoliator for skin and when applied to the skin, such provides benefits such as decreasing acne, increasing hydration, balancing or adjusting chemical parameters within the body. The use of Epsom salts are believed to aid in exfoliation and promotion of new skin cell growth which allows skin to become softer to the touch and generally have a better tactile feel.

Other types of chemical salt compositions are known to be used in baths and for skin including various sea salts and botanicals. Himalayan salt mixtures may include, for example, calcium, magnesium, potassium, copper and iron.

PRIOR ART

Chemical salt compositions such as Epsom salts are known for having beneficial results in improving the health of users. In prior art uses of Epsom salts, the chemical salt compositions have been generally put into bath water to permit the user to bathe in the presence of an aqueous solution of chemical salt compositions and water. However the use of Epsom salts simply being inserted into bath water does not permit a controlled amount of the Epsom salts to be transdermally passed into the user's body. Additionally the use of Epsom salts in bath water does not permit the interfacing of the Epsom salts or other chemical salt compositions to be interfaced with the user's body for a specified time interval to obtain the maximum effects of the salt ions.

Additionally when chemical salt compositions are used in conjunction with a bathtub containing both the water and the chemical salt composition, it is impossible to target specific areas of the user's body which will benefit the most from the salt ions introduced transdermally.

There are no known chemical salt dispensing mechanisms which are adapted to be used in conjunction with a standard shower head to permit a controlled amount of chemical salt composition to be transdermally passed into a user's body while the user is taking a shower.

Thus there is a long felt need to provide a dispensing system which can contain a specific amount of a chemical salt solution and dispense such in a controlled manner with respect to flow rate, and the amount of chemical salt solution being applied during a specified time interval.

SUMMARY OF THE INVENTION

This invention relates to a dispensing system for dispensing salt solutions transdermally to the human body.

The subject invention is directed to the system for dispensing controlled and selective amounts of chemical salt compositions to the human body and includes a tubular container extending in a vertical direction having a proximal end and a distal end. The tubular container includes a side wall extending between the distal and proximal ends of the tubular container. At least a first sieve member or shelf member is mounted to a side wall of the tubular container between the distal end and the proximal end of the tubular container. The first sieve or shelf member has a plurality of through openings passing there through and is mounted within the tubular container below a salt composition chamber formed within the tubular container between the first sieve or shelf member and the proximal end of the tubular container for containment of a chemical salt composition.

In one form of the invention, at least a second sieve or shelf member is mounted to the side wall of the tubular container below the first sieve or shelf member defining a mixing flow chamber and having a number or plurality of second sieve or shelf through openings passing through the second sieve or shelf member. In the overall concept of the dispensing system, such includes a first chemical salt composition chamber above a first sieve or shelf member and a second mixing flow chamber below the first sieve member and above a second sieve member for permitting mixtures of water and chemical salt compositions to flow out of the dispensing system onto the body of a user at a predetermined rate.

Both the first sieve or first shelf member and the second sieve or second shelf member of the dispensing system include respective through openings where the number of through opening of the first shelf member is less than the number of openings of the second shelf member.

An object of the subject dispensing system is to provide a source of chemical salt compositions and in particular Epsom salt solutions along with possible essential oils to be applied to a user which permits the user to have a higher and/or a controllable concentration of Epsom salt applied to the body such than would occur in a bathtub which includes the bath water, possible essential oils and the chemical salt composition.

Still further, it is an object of the subject system to provide a source of Epsom salts to the body of the user in a controlled manner at a controllable rate of flow.

It is a further object of the subject system to provide a source of chemical salt compositions to a user in a container having a weight which is of a nature that the system can be manually held and manipulated.

Further it is an object of the subject system to provide a dispensing system which is collapsible subsequent to use for transportability in a minimum volume.

It is a further object of the subject dispensing system to provide a source of Epsom salt solution to a user which is portable and may be used without a bathtub and easily coupled or connected to a showerhead.

It is a further object of the subject dispensing system to provide a chemical salt composition which is portable, lightweight, collapsible and able to be easily transported.

It is a further object of the invention to provide a source of Epsom salt and essential oil solutions to a user's body which provides a more controllable concentration of the Epsom salt/essential oils to be applied to the user's body than would be attainable in a bath tub.

It is a further object of the subject system to provide a source of Epsom salt solution to increase magnesium intake to address magnesium deficiencies which has occurred in a user.

It is a further object of the subject system to provide a source of Epsom salt solutions to a user which allows for essential oils or other additives to be combined with or used in the place of an Epsom salt solution.

BRIEF DESCRIPTION OF THE DRAWINGS

FIG. 4 is an embodiment of the dispensing system which provides for a shelf having a port below the chemical salt composition chamber and in fluid communication with a conduit to a flow handle for passage of fluid there through;

DETAILED DESCRIPTION OF THE PREFERRED EMBODIMENTS

Figure 6:
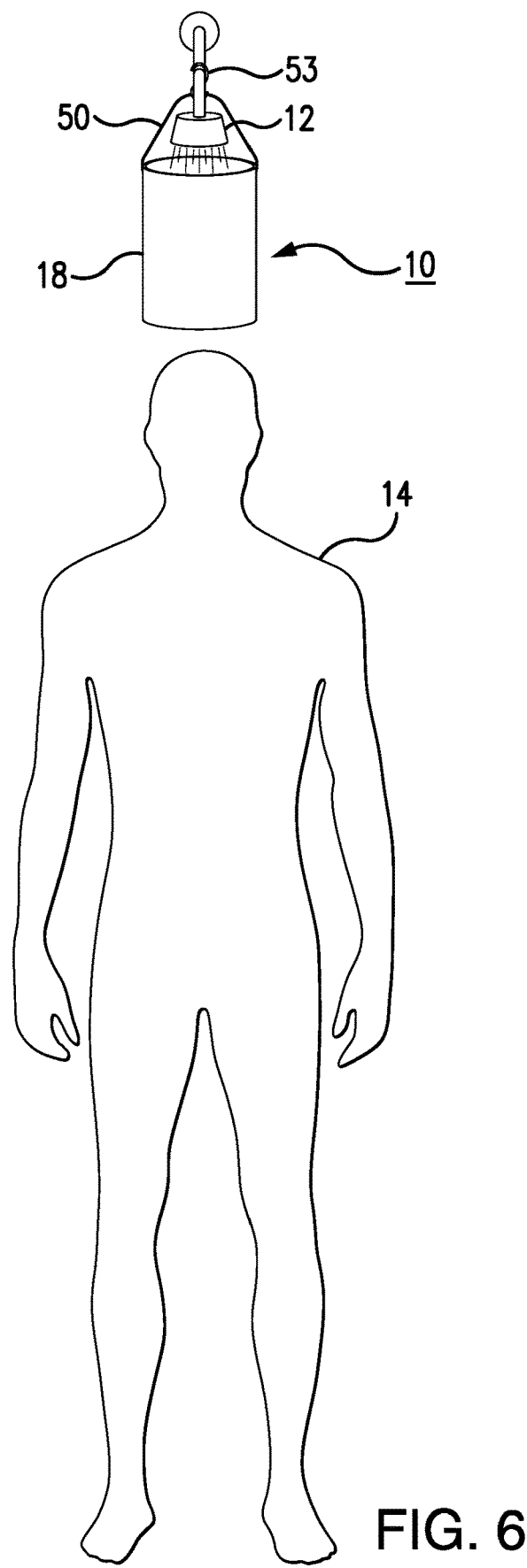
FIG. 6 is a schematic view of the system adapted to be mounted to a showerhead for passage of the solution to the user's body.

Referring now to FIGS. 1, 3, 6 and 7 there is shown a dispensing system 10 for controlled and selective dispensing of chemical salt compositions onto the human body 14. In overall concept, as shown in FIG. 6, dispensing system 10 may be mounted on a shower head 12 above user 14 and upon actuation of the shower head for dispensing water, such water flows into a chemical salt composition 16 which at least partially fills tubular container 18 as shown for example in FIGS. 1, 3, 4 and 9 to be further discussed in the following paragraphs.

In general, tubular container 18 is adapted to have inserted therein chemical salt composition 16 and possibly other essential oils which will have liquid passing there through for eventually striking the body of user 14 where some of the salt composition components will be absorbed into the body of user 14.

Figure 1:
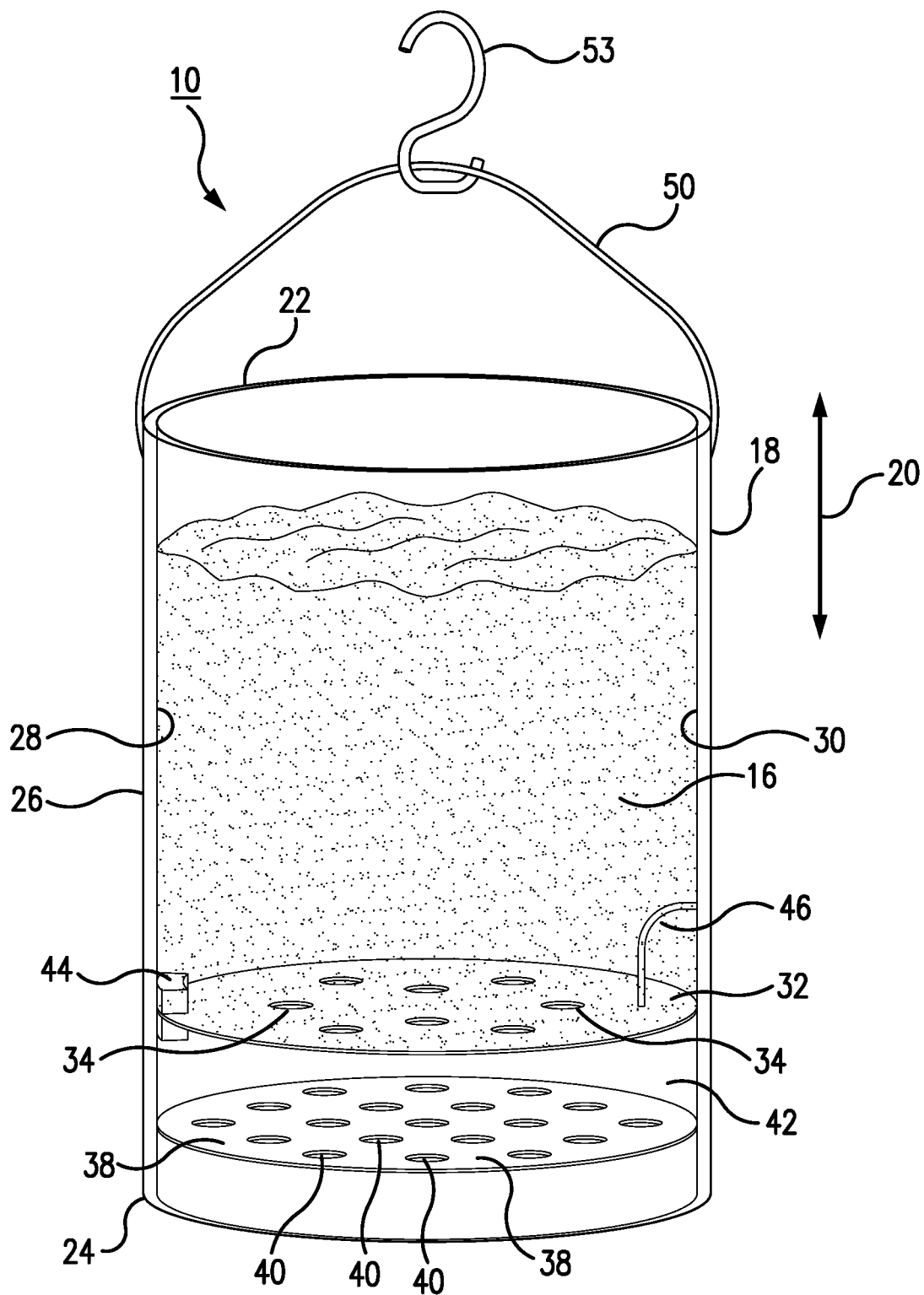
FIG. 1 is a schematic drawing showing a dispensing system having two vertically displaced sieve or shelf members beneath a chemical salt composition chamber containing the chemical salt composition.

Referring to FIG. 1, there is shown tubular container 18 ascending in vertical direction 20. Tubular container 18 includes proximal end 22 and distal end 24, where proximal end and distal ends 22 and 24 are on opposing ends of tubular container 18 when taken with respect to vertical direction 20. Tubular container 18 in certain embodiments may be formed of a somewhat flexible material such as silicone which has the ability of maintaining the semi-rigid tubular shape during use, but also may be collapsed prior to and subsequent to use in order to reduce the volume of the entire dispensing system to permit transportability in a minimum volume. Alternately tubular container 18 may be formed of a plastic polymer or other structural material which is lightweight in nature and can accept the load bearing of material contained within the tubular container 18.

As can be seen for example in FIG. 1, tubular container 18 is formed of a tubular side wall 26 extending in vertical direction 20 with a tubular container side wall inner surface 28. A first sieve or shelf member 32 is positioned and mounted in releasable contact with first tubular side wall inner surface 28. First shelf 32 is releasably mounted to the tubular container side wall inner surface 28 between the distal end 24 and the proximal end 22 of the tubular container 18. Releasable mounting of first shelf 32 may be effected through a number modes such as the insertion of first shelf member between a pair of vertically displaced lug members 44 formed on tubular sidewall inner surface at one transverse end of first shelf member 32, in combination with a tether 46 on an opposing transverse end of first shelf member 32. The tether 46 may be secured to both the tubular sidewall 26 and the first shelf member 32 on opposing ends respectively. In other aspects, as will be discussed in later paragraphs, shelf member may be mounted on a ring element which extends around the inner periphery of tubular container 18.

First sieve or shelf 32 has a plurality of through openings 34 passing through sieve 32 in substantially vertical direction 20 to permit the water activated chemical salt composition 16 to pass there through into mixing flow dispensing chamber 42. First sieve or shelf 32 may be fabricated from a plastic polymer and may be formed in particular from silicone. In general shelf 32 when formed of a silicone type polymer is formed of a more rigid or harder silicone than the sidewalls of tubular container 18 in order to maintain the structural shape of the tubular contain 18 when the first shelf 32 is mounted therein.

In this manner, chemical salt composition 16 may be maintained in salt composition chamber 30 and dispensed in a controlled manner through the first sieve through openings or holes 34. The salt composition chamber 30 is formed within said tubular container 18 between the first sieve member 32 and the proximal end 22 of the tubular container 18 for containing the chemical salt composition 16 as is seen in FIG. 1.

Dispensing system 10 permits the chemical salt composition 16 to be dispensed onto the body of the user 14 as depicted in FIG. 6. The salt composition chamber 30 permits the chemical salt composition 16 to be mixed with water and permits the user 14 to fill the chamber 30 to a point that the top of the chemical salt composition 16 is below the proximal end 22 of tubular container 18.

Tubular side walls 26 are generally formed in an extended tubular length along vertical direction 20. As previously detailed tubular container 18 may be formed of a flexible type of material such as silicone to allow reversible collapsing of tubular container 18. A silicone structure is generally found to be structurally stable and able to accept the force loading of the chemical salt composition 16. It is to be understood that tubular container 18 may be formed of a rigid material such as metal, steel, or some like material capable of accepting the force loads imparted thereto. However, in the preferred embodiment, tubular container 18 is formed of a flexible material which will allow tubular container 18 to be formed and collapsed into a compact volume during transportation.

In overall cross sectional depiction, tubular container 18 may be circular, oval, or a parallelepiped contour for accepting the chemical salt composition 16.

Additionally, tubular container 18 may have a contour which is cylindrical in nature and tapers from proximal end 22 to distal end 24. Tapering of side walls 26 provide for a more directed application of the mixture of the chemical salt composition and water which is being applied to the body of the user 14. Dispensing system 10 in a cylinder type contour has a diameter at distal end 24 which is less than the diameter at proximal end 22 of tubular container 18 in a manner such that the diameter of tubular container 18 at distal end 24 may measure approximately 4.0 inches where the proximal end 22 of tubular container 18 may be in the area of 4.25 inches. This corresponds to a circumference for a cylindrically contoured tubular container 18 to approximate a circumference of 13.0 inches and the lower section or distal end point 24 has a circumference of approximately 12.5 inches. Overall vertical length of tubular container 18 generally approximates 7.0 inches. This type of configuration will provide for a tapering included angle of approximately 10.28 degrees.

Figure 2A:
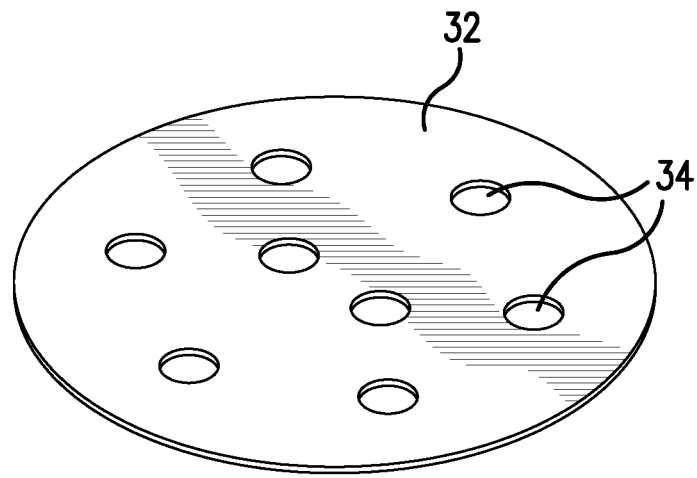
FIG. 2A is a schematic drawing showing a first sieve or shelf member having through holes.
Figure 2B:
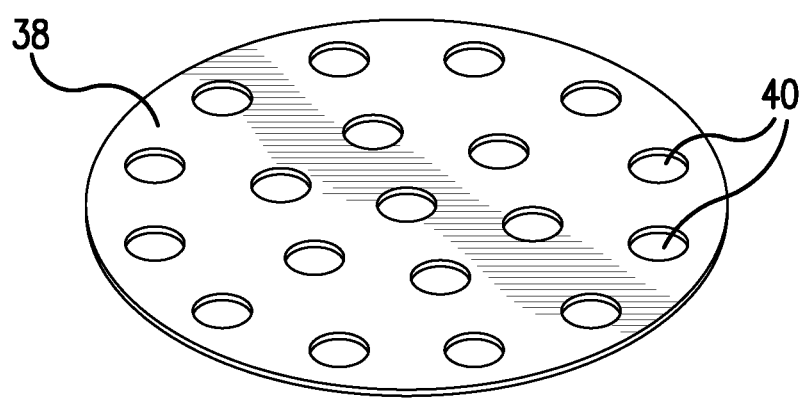
FIG. 2B is a schematic drawing of a second sieve or shelf member having a larger number of through openings than the first sieve member and mounted below the first sieve member as shown in FIG. 2A.
Figure 3:
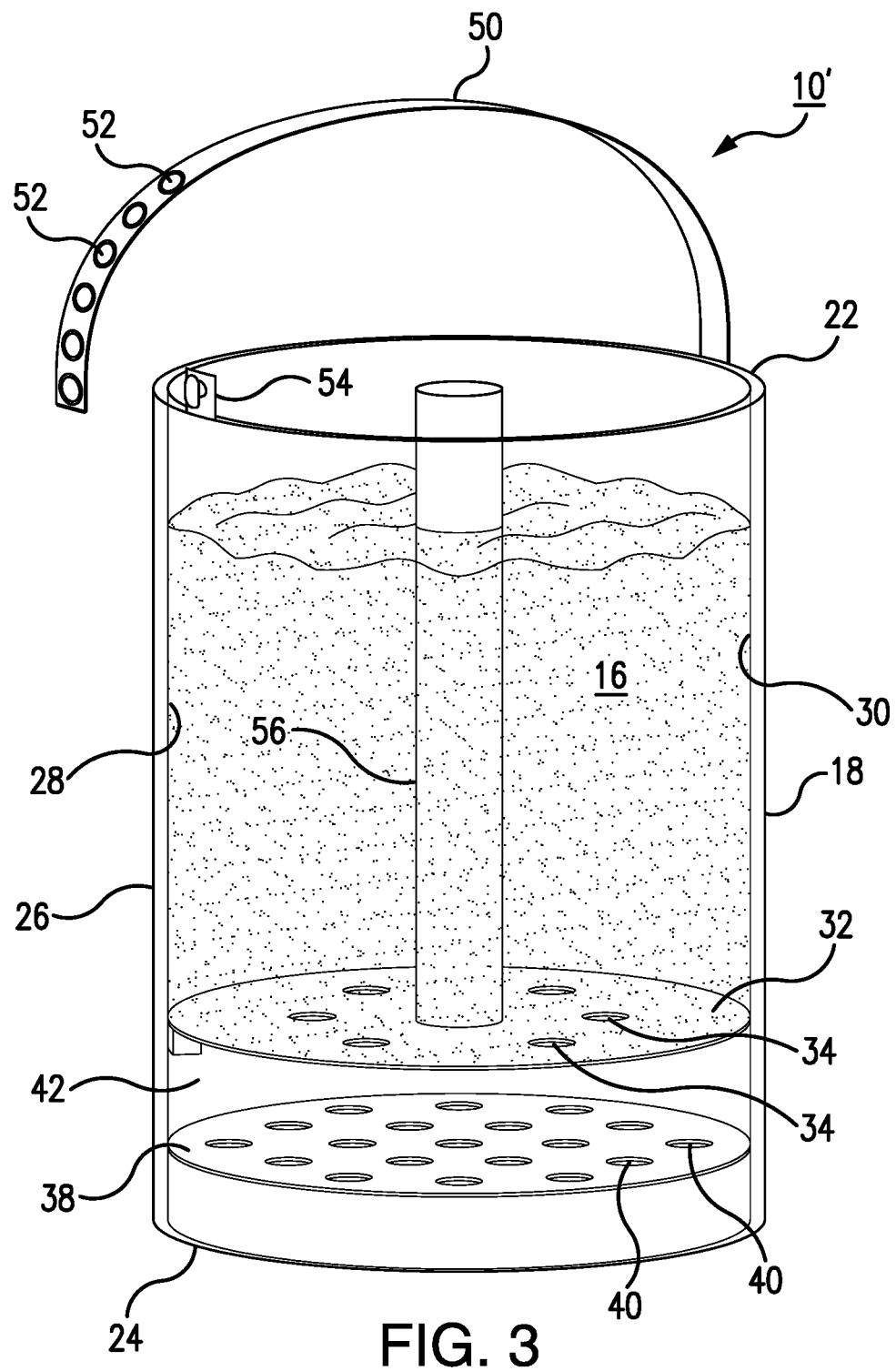
FIG. 3 is a schematic drawing of the chemical salt composition dispensing system showing a rod member attached to the first shelf or first sieve member for allowing removal or vertical displacement of the first sieve member with respect to a tubular container within which it is mounted, and a fastening member allowing the dispensing system to be mounted to a showerhead.

Turning now to FIGS. 1-3, dispensing system 10 may have a second sieve or shelf member 38 mounted to the inner surface of side wall 28 below the first sieve member 32. The first sieve member 32 and the second sieve member 38 define a mixing flow chamber 42 therebetween. Second sieve member 38 includes a plurality of second sieve through holes 40 for dispensing of the chemical salt composition and water mixture onto user 14. Second sieve or shelf member 38 may also be formed of a silicone polymer material or in the alternative may be formed of a more rigid material to further reinforce the structural contour of the tubular container 18 when in use.

The first sieve member 32, as is seen in FIG. 1, may be mounted between mounting lug members 44 on one side and possibly attached to the tubular side wall inner surface 28 through a connection tie or tether 46. Connection tie 46 may simply be a string or other type of cord like member which is attached to first sieve member 32 on one end and to tubular side wall inner surface 28 on an opposing end as is seen in FIG. 1.

Both first sieve members 32 and second sieve member 38 are formed of a somewhat flexible material such as silicone. However, it is generally necessary that both sieve members 32 and 38 are formed of a material which is less flexible than the tubular side walls 26 in order to permit structural acceptance of the force loads applied when the chemical salt composition 16 is within salt composition chamber 30. In fact, second sieve member 38 may be formed of a rigid material such as close cell plastic, metal or some other rigid type material which will conform and maintain the tubular side walls 26 in a more rigid manner to accept the loads associated with chemical salt composition 16 subsequent to insertion into salt composition chamber 30.

Second sieve member 38 is mounted to tubular side wall inner surface 28 above tubular container distal end 24. Second sieve member 38 is thus mounted within tubular container 18 below first sieve member 32 and above distal end 24 of tubular container 18. As seen in FIG. 2, first sieve member 32 includes a plurality of first sieve member through hole openings 34 which are substantially sized to be equal to the second sieve member through holes 40. In one embodiment, the through openings 34 and 40 may be approximately 1 mm in diameter. It is important that the integer number of first sieve through openings 32 be less than the integer number of second sieve through openings 40. In this manner, the chemical salt composition and water mixture 16 will then trickle out slowly through the first sieve member 32 due to the fewer openings 34 in the first sieve member 32 with respect to the through openings 40 in the second sieve member 38. With the use of fewer holes or openings 34 in first sieve member 32 with respect to second sieve member 38, the water and chemical salt composition will have a longer period of time to remain in the salt composition chamber 30 and to allow further dissolving of the salt in the water. With the additional hole openings 40 in the second sieve member 38, the combination of the chemical salt composition and water is permitted to flow through the second sieve member 38 and provide an even distribution onto the user 14.

The dispensing system 10 may include a first shelf ring member 48 secured to the inner surface 28 of the tubular side wall 26 with the first shelf ring member 48 extending throughout the perimeter of the inner surface 28 of tubular sidewall 26.

Referring once again to FIG. 1, there is shown dispensing system 10 having a positioning member 50 secured and coupled to opposing laterally displaced ends of proximal end 22 where positioning member 50 is adapted to hang the tubular container 18 on a shower head 12 schematically shown in FIG. 6. Additionally, positioning member 50 includes a clip member 53 for mounting tubular container 18 in a releasable coupling to the shower head 12. As seen in FIG. 3, positioning member 50 may include a number of displaced positioning member openings 52 with fastening hook 54 coupled and securely mounted to proximal end 22 of tubular container 18. In this manner, positioning member 50 may be mounted as differing heights from shower head 12 at the desirability of the user 14. In this manner, dispensing system 10' is height adjustable with respect the body of user 14 as required.

In this manner, with the displaced openings 52 formed through positioning member 50, such permits adjustability of height between shower head 12 and tubular container 18 in a simple and easy manner.

Positioning member 50 may be a strap formed of flexible plastic, textile or other like material not important to the system concept as herein described with the exception that the strap or positioning member 50 be able to accept the structural loads imparted by the weight of the chemical salt composition 16 within salt composition chamber 30 and not be chemically reactive with respect to the composition 16.

As shown in FIG. 3, dispensing system 10' may include rigid rod member 56 secured to first sieve or shelf member 32 on one end thereof. Securement of rigid rod member 56 to first sieve member 32 may be through bolting, adhesive securement or other like technique. First sieve rigid rod member 56 is fixed to the upper surface of first sieve member 32 and extends into chemical salt composition chamber 30 to permit first sieve member 32 to be vertically displaceable and allow removal or partial removal of first sieve member 32. In this manner, when user 14 wishes to remove some or all of chemical salt composition 16, the user 14 simply grasps the end of the rod 56 near proximal end 22 of tubular container 18 and pulls up on rod 56 for removal or partial displacement of first shelf member 32 with respect to tubular member 18.

Figure 4:
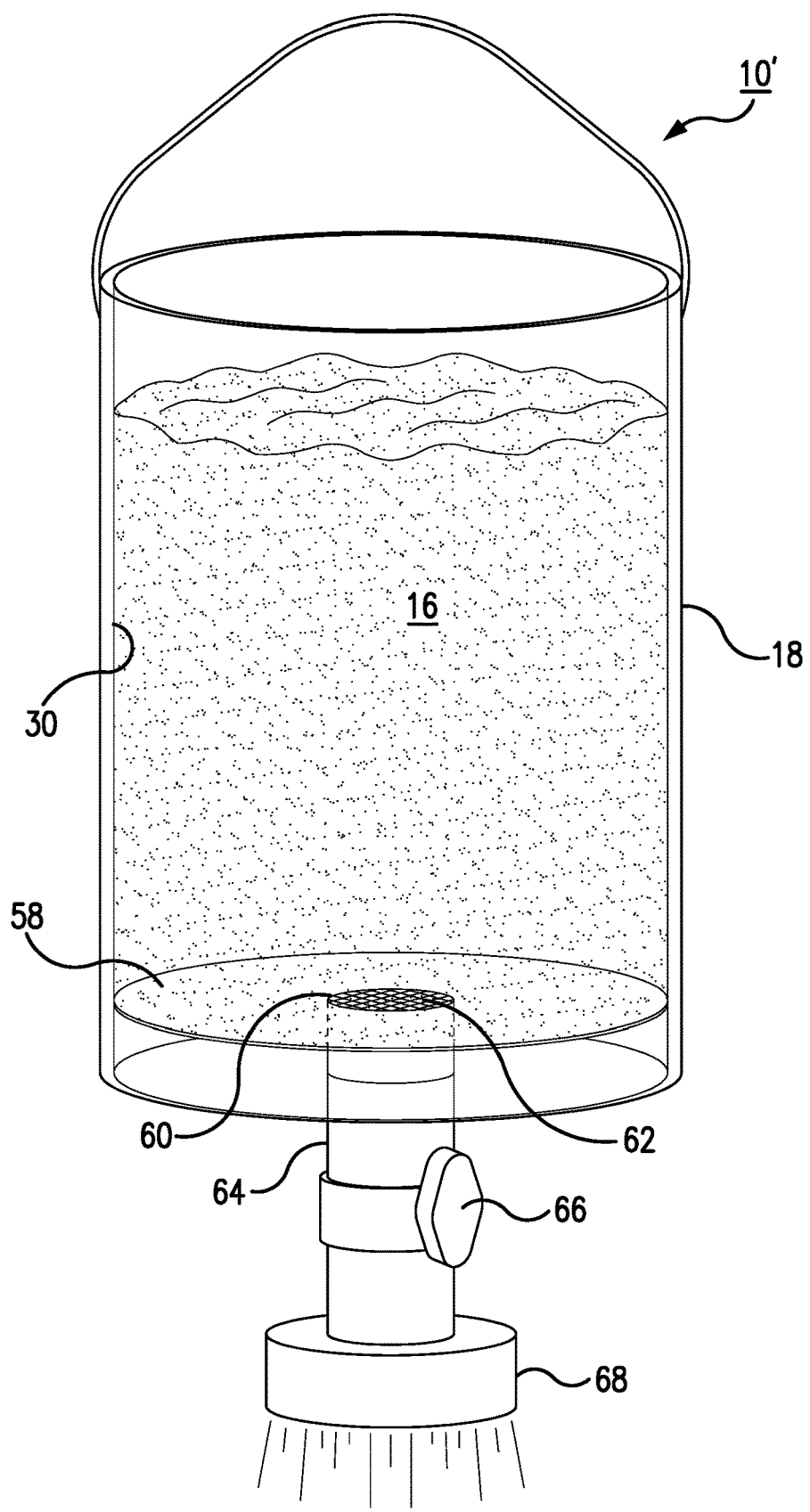

Referring now to FIG. 4, there is shown dispensing system 10" which has a singular disc member 58 mounted above distal end 24 of tubular container 18. Disc member 58 includes a central port area 60 defining a through opening of disc member 58. Central port member 60 may have a mesh covering 62 to allow flow distribution from salt composition chamber 30 into conduit 64 for passage through handle 68 having openings formed there through for distribution of the chemical salt composition and water mixture onto the user 14. Control valve 66 may be formed in the conduit 64 for permitting control of dispensing fluid. In this manner, dispensing system 10" includes mixing/containment chamber 30 where chemical salt composition 16 and water are substantially mixed. This embodiment shows the output port 60 formed on the shelf member or disc member 58 with the outflow port 60 being in fluid communication with the conduit 64 which terminates at a distal end in the handle 68 having holes passing there through which allows the mixture to pass onto the body of the user 14.

Control valve 66 may be one of a number of hand operated control valves which are commercially available, the control valve 66 is used to control fluid flow through conduit 64 by essentially varying the size of the flow passage through the conduit 64. By rotating the end member of the control valve 66 to a desired angle, the user is able to control the amount of liquid flowing to the handle 68.

Handle 52 may be a rubber or plastic ring formation with holes in the bottom for allowing the mixture to be dispensed over the cross sectional area of the bottom of the handle 68. The regulator or control valve 66 is mounted intermediate the opposing ends of conduit 64 and can be regulated to terminate flow or provide a controlled amount of flow rate of the mixture.

Figure 7:
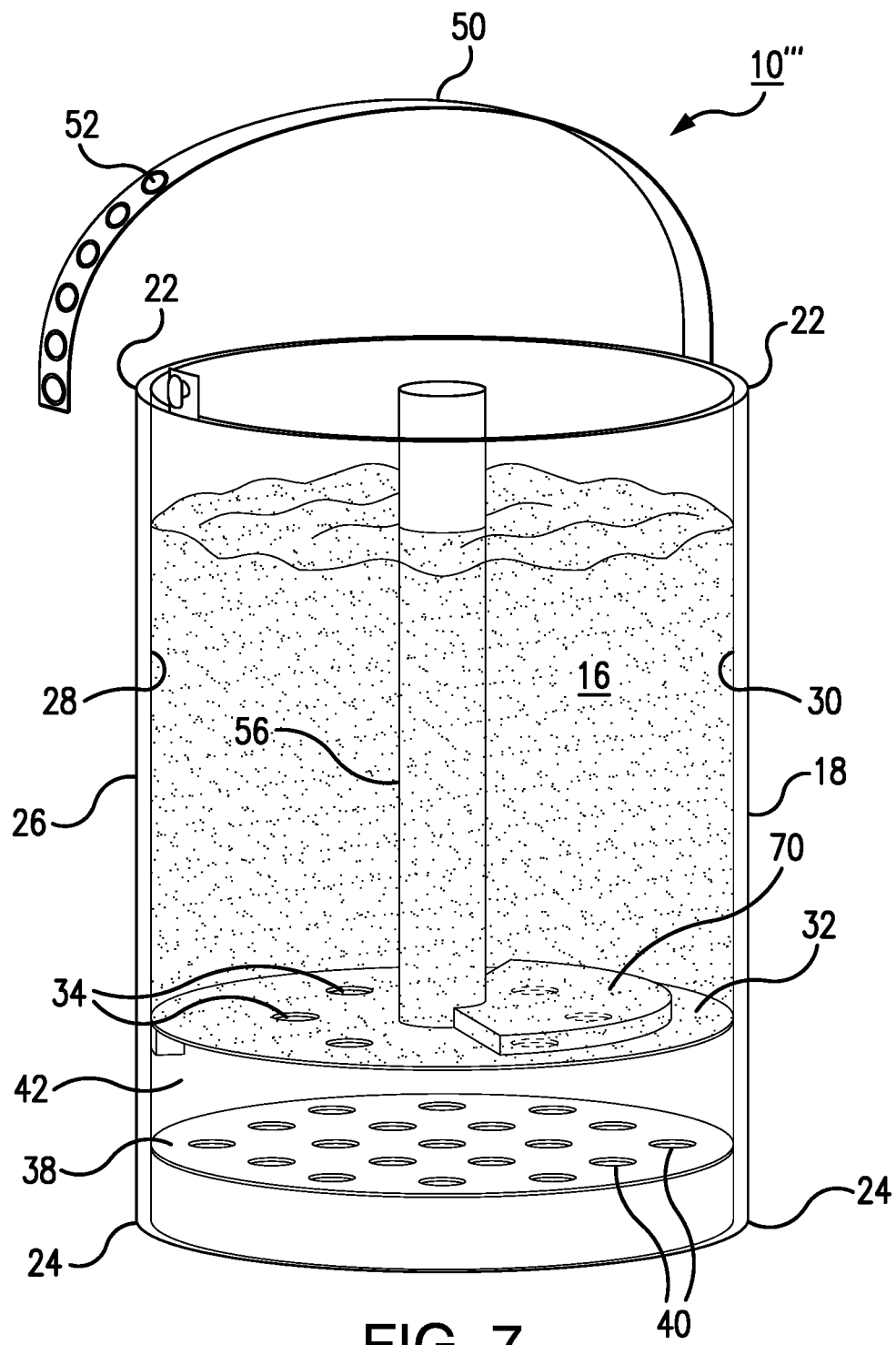
FIG. 7 is a schematic view of the chemical salt composition dispensing system which includes a control mechanism to open or close predetermined through openings in the first shelf member for controlling the flow rate through the first shelf member.

Referring now to FIG. 7, there is shown dispensing system 10'" which includes rod member 56 coupled to first sieve member 32 on one end thereof within tubular container 18 as previously discussed. In this embodiment, there is added flow control mechanism 70 which is slidably interfacing with an upper surface of first sieve or shelf member 32. The flow control mechanism 70 may be a sliding solid portion or element which is able to cover one or more of the through openings 34 in order to control fluid flow through first sieve member 32 into chamber 42 and then through the openings 40 as previously described.

In this manner, a predetermined number of first sieve through openings 34 can be opened for flow there through wherein the flow rate is controllable by the user 14.

Figure 5:
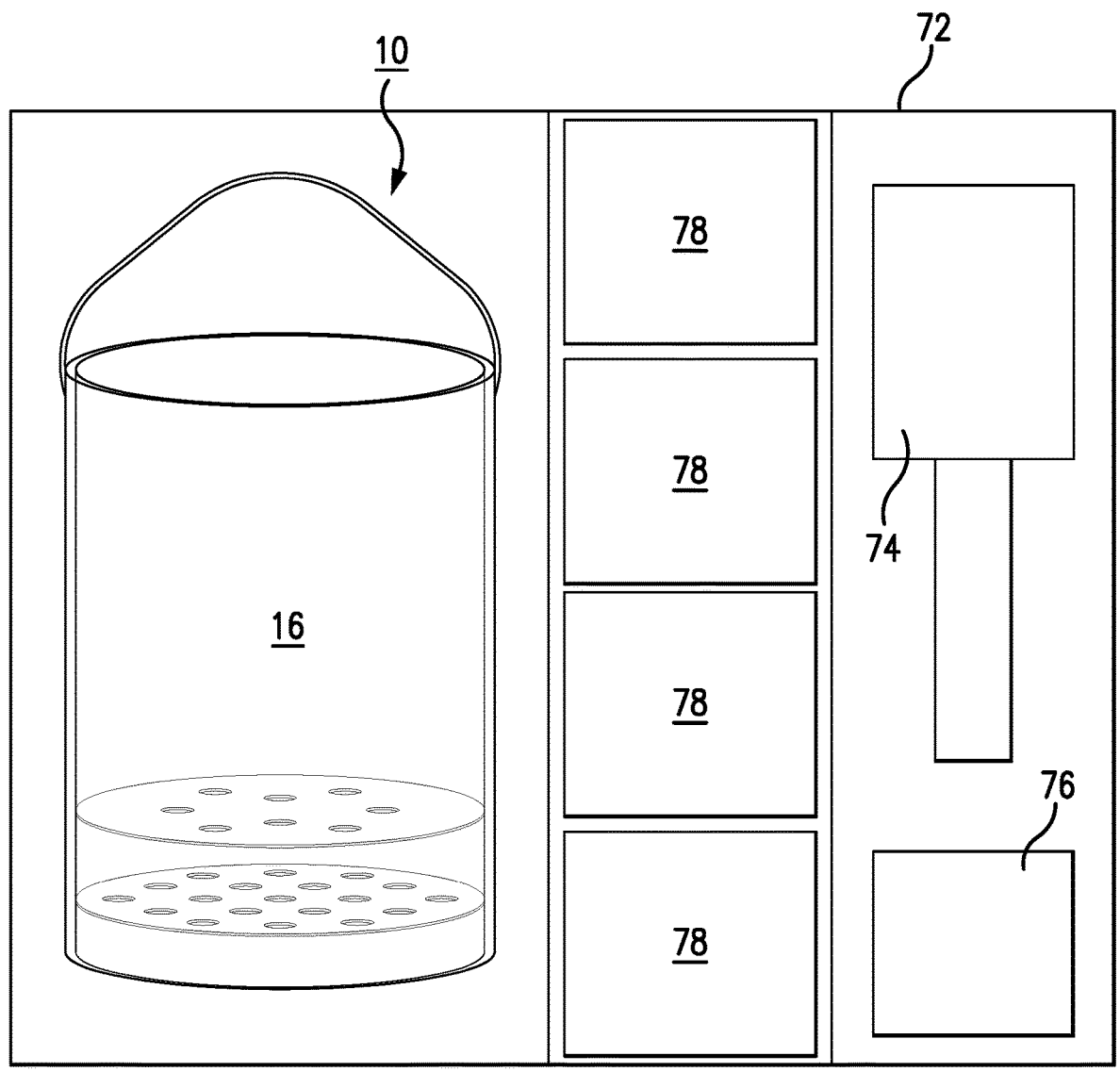
FIG. 5 is a schematic representation of a boxed kit which permits storage and transportation of a chemical salt composition system, a plurality of chemical salt composition packets, a brush and instructions for use.

Referring now to FIG. 5, there is shown schematically a kit for the chemical salt composition container dispensing system 10 wherein there is boxed a brush 74 and instruction manual 76, a plurality of chemical salt composition packets 78 and the dispensing system 10. The packets 78 may contain a measured amount of chemical salt composition appropriate for a single use. As an example, the dispensing system 10 is filled with approximately 945 ounces of water and each packet uses 94 ounces of salt providing substantially a one to ten concentration. It is known that transdermal application may be dependent upon a number of parameters such as time of application, strength/concentration of the chemical salt composition and other parameters including flow rate. The amount of composition within the composition packets is generally sized to permit evacuation of the mixing chamber to be within 1.0 to 4.0 minutes under normal shower flow rates of 1 to 2.5 gallons per minute.

Brush 74 may be used for exfoliation which may provide advantages relating to increasing transdermal penetration of salt ions. Instruction manual 76 may be included in the boxed kit 72 to provide instructions to the user either in paper form or DVD or other electronic medium.

Figure 8:
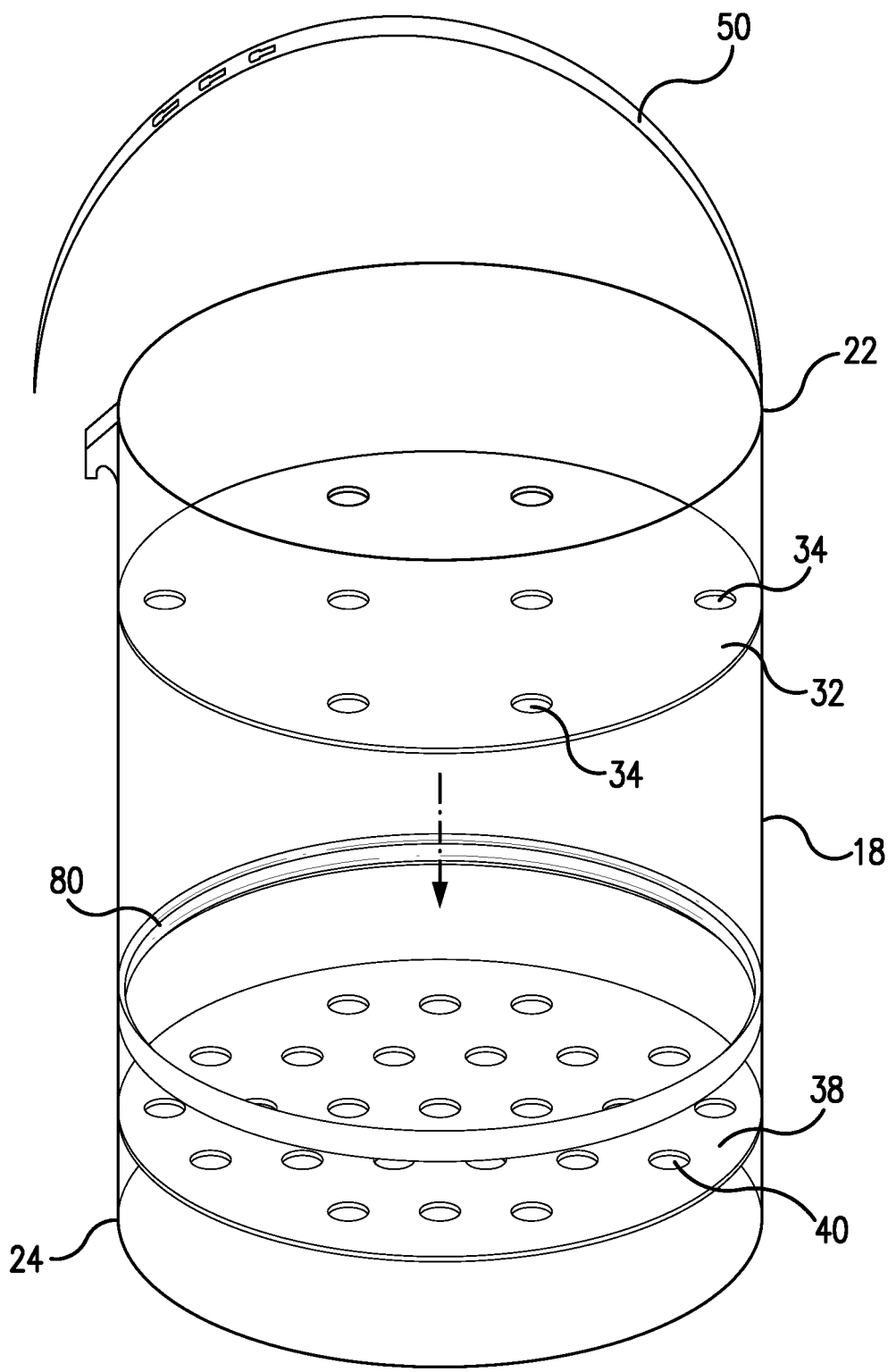
FIG. 8 is a schematic drawing showing a ring member extending around the periphery of an inner wall of the tubular container upon which the first shelf or sieve member is mounted.

Referring to FIG. 8, there is depicted an embodiment of the dispensing system 10 where a mounting ring 80 is secured to the inner tubular sidewall inner surface for mounting thereon the first shelf 32. The mounting ring 80 may be formed in one piece formation with the tubular container 18 or otherwise attached through adhesive attachment, bolting or some like technique. First sieve or shelf member 32, may be inserted into tubular container 18 and mounted on mounting ring 80 to provide a structurally sufficient system to contain the composition 16.

Figure 9:
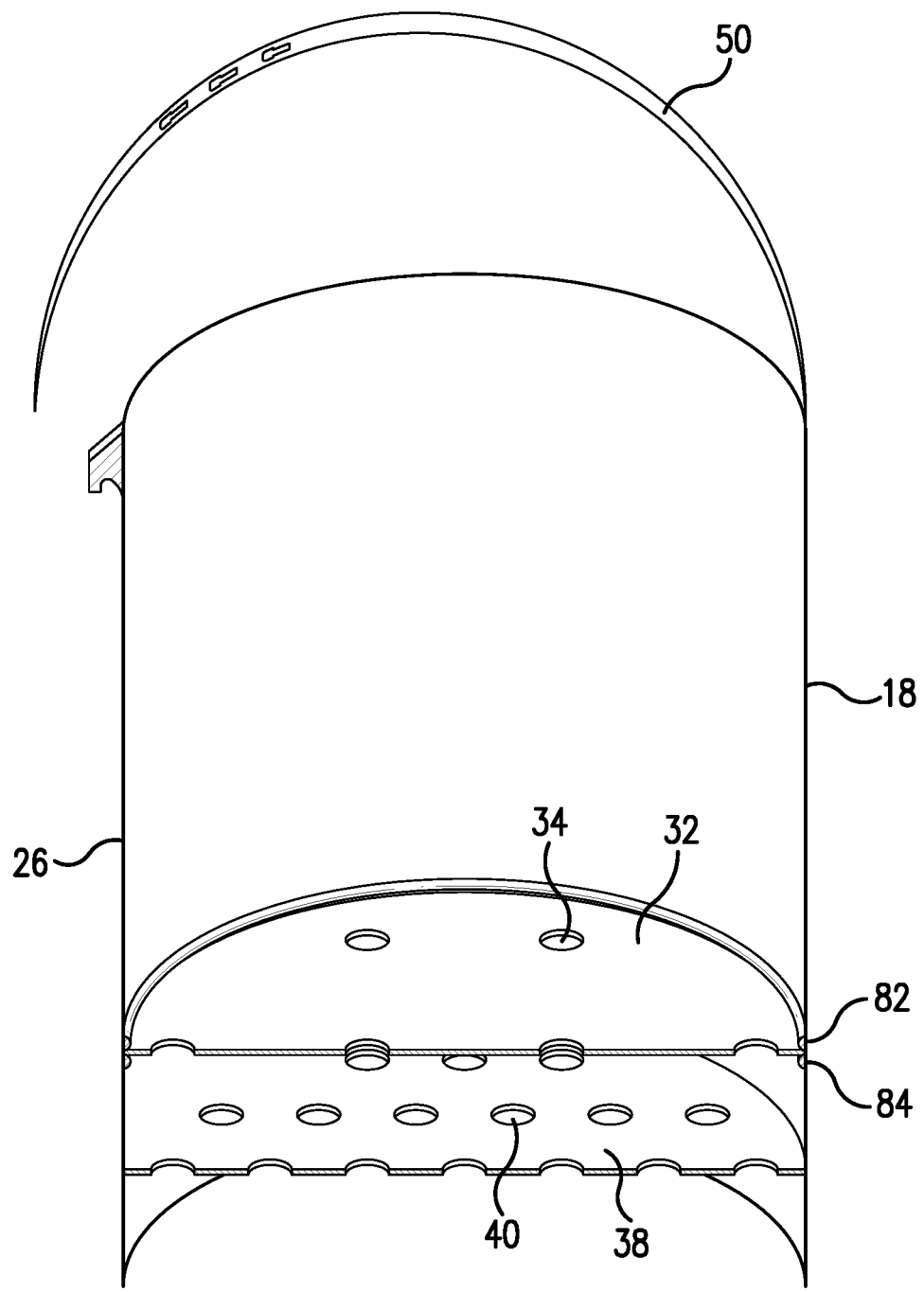
FIG. 9 is a partially cut-away view of the dispensing system showing the first and second shelf member having an arcuate contour; and, FIG. 10 is a schematic view of the dispensing system showing a tubular member having a bellows contour.
Figure 10:
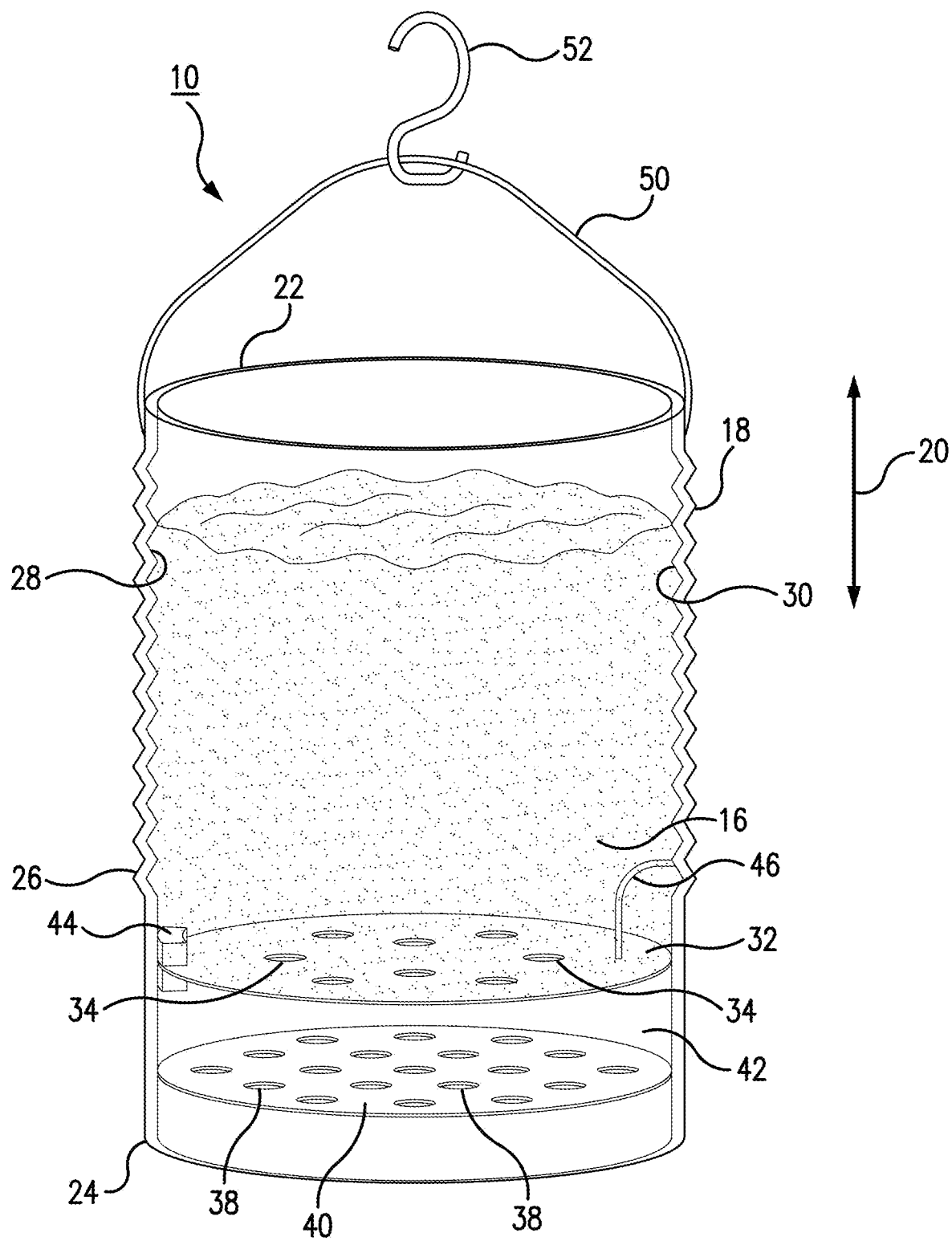

Referring to FIG. 9, there is depicted an embodiment where the first shelf 32 is deformed into an arcuate shape for mounting between either one or two ridges 82 and 84 which are located in a manner where the ridges 82 and 84 are able to capture the first shelf 32 therebetween. Since first shelf is somewhat flexible, it can be deformed when inserted into the ridges 82 and 84 to provide a compressive fore against the tubular sidewall 26 and add structural rigidity to the tubular container 18. Alternatively, there can be one ridge 82 extending around the periphery of tubular sidewall inner surface 28 where first shelf 32 is mounted thereon in a releasably fixed manner.

It is to be understood that although the preferred embodiment of the subject dispensing system is directed to dispensing controlled and selective amounts of the chemical salt compositions detailed above, the particular composition may include salt compositions, essential oils, bath pellets, scented and unscented soap, as well as soap powder and like compositions. Other types of additives such as aromatic oils and medication are contemplated by the subject dispensing system.

It is to be further understood that the tubular container in another embodiment of the subject dispensing system, may take the form of a porous bag which contains the salt composition or other substance to be applied to the body of the user. The bag may be formed of a mesh like textile or other material composition which allows the contained composition, after being impinged upon by water emitted from the shower head, to mix with and be at least partially dissolved prior to impinging on the user's body. The particular composition of the bag is not important to the inventive concept with exception that the material used be non-reactive with respect to the chemical composition within the bag. This embodiment further envisages a porous first bag at least partially filled with the composition to be applied to the user's body and a second porous bag within which the first bag is at least partially inserted. Both bags may be attached to the shower head by a releasable hook, or other fastening device which have been previously described. With this embodiment a more controlled application of the composition within the first bag can be applied to the user's body.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of elements, steps, or processes may be reversed or interposed, all without departing from the spirit or scope of the invention as defined in the appended claims.

What is claimed is:

1. A system for dispensing controlled and selective amounts of chemical salt compositions comprising:
    a tubular container extending in a vertical direction having a proximal end and a distal end, said tubular container having a sidewall extending between said distal and proximal ends, said tubular container proximal end adapted to be hung and displaced from a shower head, said proximal end of said tubular container being devoid of a watertight mechanism for securing the tubular container to said shower head;
    at least a first sieve member mounted to said sidewall of said tubular container between said distal end and said proximal end of said tubular container, said at least first sieve member having a plurality of first sieve through openings passing there through, and
    a salt composition chamber formed within said tubular container between said first sieve member and said proximal end of said tubular container for containing a chemical salt and water mixture solution of a predetermined user selected concentration;
    a flow control mechanism configured to be manually operated by a user for controlling the number of openings through which said mixture flows whereby a flow rate output from the system is controlled; and,
    a flexible and height adjustable positioning member coupled to said tubular container proximal end for selectively adjusting the distance between the tubular container and said shower head.

2. The system as recited in claim 1 including at least a second sieve member mounted to said sidewall of said tubular container below said first sieve member defining a mixing flow chamber and having a plurality of second sieve through openings passing there through.

3. The system as recited in claim 2 where said second sieve member is mounted to said tubular container sidewall above said tubular container distal end.

4. The system as recited in claim 2 where an integer number of said first sieve through openings is less than an integer number of said second sieve through openings.

5. The system as recited in claim 4 where a cross-sectional areas of said first sieve member through openings are substantially equal to the cross-sectional areas of said second sieve member through openings.

6. The system as recited in claim 2 including a first sieve member shelf mounted to an inner surface of said tubular container for releasably mounting said first sieve member to said tubular container.

7. The system as recited in claim 6 where said tubular container has a first shelf ring member secured to said inner surface of said tubular container and extending throughout the perimeter of said tubular container.

8. The system as recited in claim 2 including a rigid rod member secured to said first sieve member, said rigid rod member fixed to an upper surface of said first sieve member and extending into said salt composition chamber to permit said first sieve member to be removed from internal said tubular container.

9. The system as recited in claim 1 wherein the flexible and height adjustable positioning member is coupled to opposing ends of said tubular container proximal end and adapted for hanging said tubular container on a shower head.

10. The system as recited in claim 9 including:
    (a) a fastening hook coupled to said proximal end of said tubular container; and
    (b) a plurality of displaced openings formed through said flexible and height adjustable positioning member adapted to adjust the height between said shower head and said tubular container.

11. The system as recited in claim 10 where said flexible and height adjustable positioning member is a strap member.

12. The system as recited in claim 11 where said flexible and height adjustable positioning member includes a clip member secured to said flexible and height adjustable positioning member and is adapted to be releasably secured to said shower head.

13. The system as recited in claim 1 where said tubular container has a cross-sectional contour selected from the group of; a parallelepiped, tubular container, a cylindrical tubular container, or an oval cross-sectionally tubular contour.

14. The system as recited in claim 1, where said tubular container is a bellows shaped contour to permit collapsing of said tubular container.

15. The system as recited in claim 1 where said tubular container is sized to permit the volume of chemical salt composition within said salt and water mixture solution to be dispersed within a time interval of 1.5-3.0 minutes.

16. The system as recited in claim 1 where said first sieve member includes a central portion containing said first sieve through openings.

17. The system as recited in claim 16 where said central portion is formed as a mesh.

18. The system as recited in claim 17 where said central portion is in fluid communication with a conduit having a first end secured to said central portion.

19. The system as recited in claim 18 including a handle member secured to a second end of said conduit, said handle member having a plurality of through openings for dispensing of the chemical salt and water mixture solution.

20. The system as recited in claim 19 including a control valve member formed within said conduit for controlling the rate of flow of said chemical salt and water mixture solution through said conduit.

21. The system as recited in claim 1 wherein the flow control mechanism is slidable on an upper surface of said at least first sieve member for providing a predetermined number of said first sieve through openings to be opened for flow there through whereby a flow rate may be controlled.

* * * * *